United States Patent
Park et al.

(10) Patent No.: US 6,998,498 B2
(45) Date of Patent: Feb. 14, 2006

(54) AMINOCYCLOPENTADIENYL RUTHENIUM COMPLEXES AND PREPARATION THEREOF

(75) Inventors: Jaiwook Park, Kyungsangbuk-do (KR); Mahn-Joo Kim, Kyungsangbuk-do (KR); Jun Ho Choi, Kyungsangbuk-do (KR); Yangsoo Ahn, Seoul (KR)

(73) Assignee: Postech Foundation, (KR)

( * ) Notice: Subject to any disclaimer, the term of this patent is extended or adjusted under 35 U.S.C. 154(b) by 0 days.

(21) Appl. No.: 10/507,444

(22) PCT Filed: May 17, 2002

(86) PCT No.: PCT/KR02/00925

§ 371 (c)(1),
(2), (4) Date: Sep. 13, 2004

(87) PCT Pub. No.: WO03/076449

PCT Pub. Date: Sep. 18, 2003

(65) Prior Publication Data

US 2005/0209473 A1    Sep. 22, 2005

(30) Foreign Application Priority Data

Mar. 14, 2002 (KR) ................. 2002-13809

(51) Int. Cl.
*C07F 17/02* (2006.01)
*C07C 29/74* (2006.01)
(52) U.S. Cl. ..................... 556/137; 568/913
(58) Field of Classification Search ......... 556/137; 568/913

See application file for complete search history.

(56) References Cited

OTHER PUBLICATIONS

Daran et al., Organometallics, vol. 3, No. 8, pp. 1158-1163 (1984).*
Ayllon et al., Organometallics, vol. 18, No. 20, pp. 3981-3990 (1999).*
Casey et al., organometallics, vol. 21, No. 23, pp. 5038-5046 (2002).*
Choi et al., Angew. Chem. Int. Ed., vol. 41, No. 13, pp. 2373-2376 (2002).*

* cited by examiner

*Primary Examiner*—Porfirio Nazario-Gonzalez
(74) *Attorney, Agent, or Firm*—Anderson Kill & Olick, PC

(57) ABSTRACT

Novel aminocyclopentadienyl ruthenium complex is useful as a catalyst in the racemization of a chiral compound.

11 Claims, No Drawings

AMINOCYCLOPENTADIENYL RUTHENIUM COMPLEXES AND PREPARATION THEREOF

FIELD OF THE INVENTION

The present invention relates to a novel ruthenium complex which is a remarkably effective catalyst in the racemization of chiral compounds.

BACKGROUND OF THE INVENTION

The production of one enantiomeric form of a chiral compound is often required in the pharmaceutical and other chemical industries and the desired enantiomer is obtained via resolution of its racemate. In such a process it is essential from the economic point of view to convert the unwanted enantiomer back to the racemic form and recycled.

In the racemization step, ruthenium complexes such as [(p-cymene)RuCl$_2$]$_2$ and ($\eta^5$-Ph$_4$C$_4$CO)$_2$H($\mu$-H)(CO)$_4$Ru$_2$ (Shvo catalyst) are used as a catalyst. However, the ruthenium cymene complex exhibits a slow racemization reaction at room temperature, and Shvo catalyst which exists in the form of a dimer must be activated at a high temperature and it also requires the use of a hydrogen-transfer agent, e.g., the corresponding ketone to the alcohol in case a chiral alcohol is to be racemized (Y. Shvo et al, *Organometallics*, 8, 162, 1989).

SUMMARY OF THE INVENTION

Accordingly, it is an object of the present invention to provide a novel compound which can be used as an effective catalyst in the racemization of chiral alcohols under a mild condition.

It is another object of the present invention to provide a process for the preparation of said compound.

In accordance with one aspect of the present invention, there is provided a ruthenium complex of formula(I):

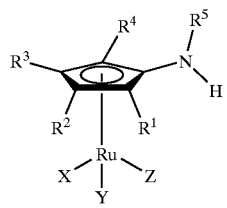

(I)

wherein:
R$^1$, R$^2$, R$^3$ and R$^4$ are each independently phenyl, substituted phenyl or C$_{1-5}$ alkyl;
R$^5$ is hydrogen, phenyl, substituted phenyl, C$_{1-5}$ alkyl, substituted C$_{1-5}$ alkyl, C$_{3-7}$ cycloalkyl, C$_{2-5}$ alkenyl or C$_{2-5}$ alkynyl; and
X, Y and Z are each independently hydrogen, halogen, carbonyl or PR$^5$$_3$.

Further, in accordance with another aspect of the present invention, there is provided a process for the preparation of the ruthenium complex of Formula(I), which comprises reacting a compound of Formula(II) and a ruthenium compound, such as Ru$_3$(CO)$_{12}$, RuCl$_2$(CO)$_2$(PR$^5$$_3$)$_2$, [RuCl$_2$(CO)$_3$]$_2$, RuCl$_2$(PR$^5$$_3$)$_3$, and RuCl$_3$ in a solution containing a haloform:

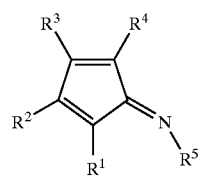

(II)

wherein:
R$^1$, R$^2$, R$^3$, R$^4$ and R$^5$ have the same meanings as defined above.

DETAILED DESCRIPTION OF THE INVENTION

In the compound of Formula(I) of the present invention, the substituent of the substituted phenyl is at least one selected from the group consisting of C$_{1-5}$ alkyl, cycloalkyl, alkenyl, alkynyl, alkoxy, halogen, nitro, nitroso, amino, aminocarbamyl, hydroxy, mercapto and C$_{1-5}$ alkylthio, and the substituent of the substituted C$_{1-5}$ alkyl is at least one selected from the group consisting of aryl, C$_{1-5}$ alkoxy, halogen, nitro, nitroso, amino, aminocarbamyl, hydroxy, mercapto and C$_{1-5}$ alkylthio.

In Formula(I) of the present invention, R$^1$, R$^2$, R$^3$ or R$^4$ is preferably a phenyl or C$_{1-5}$ alkyl group, R$^5$ is preferably hydrogen, a phenyl or substituted phenyl group, a C$_{1-5}$ alkyl or substituted C$_{1-5}$ alkyl group or a C$_{3-7}$ cycloalkyl group, and X, Y and Z substituents are each preferably hydrogen, halogen, carbonyl, or a phosphine group.

The ruthenium complex of Formula(I) of the present invention may be prepared according to Reaction Scheme A:

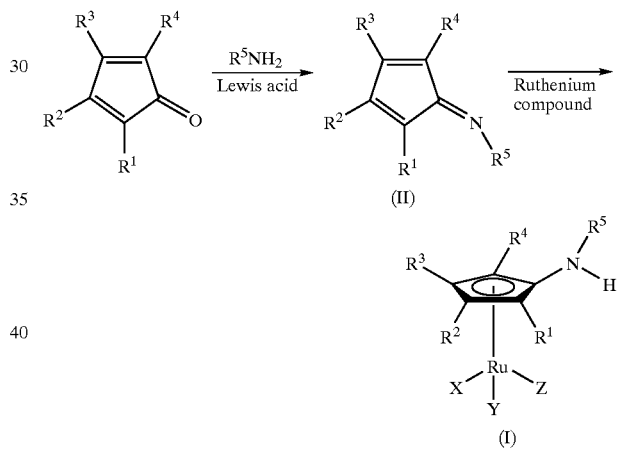

Reaction Scheme A wherein:
R$^1$, R$^2$, R$^3$, R$^4$, R$^5$, X, Y and Z have the same meanings as defined in formula(I) above.

Namely, a cyclopentadienone derivative such as tetraphenylcyclopentadienone is reacted in an aprotic solvent with a primary amine in the presence of a Lewis acid to obtain an imine compound of Formula(II)(Step 1). Then, the imine compound of Formula(II) is reacted with a ruthenium compound having X, Y and Z groups, such as Ru$_3$(CO)$_{12}$, RuCl$_2$(CO)$_2$(PR$^5$$_3$)$_2$, [RuCl$_2$(CO)$_3$]$_2$, RuCl$_2$(PR$^5$$_3$)$_3$, or RuCl$_3$ in a solvent, preferably a haloform to obtain the ruthenium complex of Formula(I) of the present invention (Step 2).

Representative examples of the primary amine used in Step 1 are ammonia, methylamine, ethylamine, propylamine, butylamine, pentylamine, isobutylamine, isopropylamine, t-butylamine, cyclopropylamine, cyclobutylamine, cyclopentylamine, aniline, toluidine and benzylamine. Also used in the present invention is a conventional Lewis acid, commonly known in the art, including TiCl$_4$, AlCl$_3$, BF$_3$ and SnCl$_4$.

Representative examples of the aprotic solvent are toluene, benzene, hexane, oxane, tetrahydrofuran, diethyl ether, diisopropyl ether, t-butylmethyl ester, ethyl acetate, acetonitrile, acetone, dichloromethane, chloroform and carbon tetrachloride.

In Step 1, the primary amine, the Lewis acid and the aprotic solvent may be used in amounts of 1 to 7 molar equivalents, 0.1 to 3 molar equivalents and 2 to 20 folds (v/v), respectively, based on the starting cyclopentadienone derivative, and the reaction may be conducted at a temperature in the range of 50° C. to 150° C.

In Step 2, the solvent may be chloroform, bromoform or fluoroform, and the amount of the imine compound of Formula(II) may be 1 to 3 mole equivalents based on the ruthenium compound. The reaction may be conducted at a temperature in the range of 40° C. to 120° C.

The ruthenium complex of Formula(I) of the present invention is useful particularly in the racemization reaction of a secondary alcohol. The racemization may be carried out by adding the complex of Formula(I) of the present invention, together with a base, to a secondary alcohol having a chiral center in an aprotic solvent and agitating the resulting mixture at room temperature for about 30 minutes under an inert atmosphere. The base may be an inorganic base such as LiOH, KOH, NaOH, tBuOK and $Na_2CO_3$ or an organic base such as triethylamine, diisopropylethylamine, DBU (1,8-diazabicyclo[5.4.0]undec-7-ene), DBN (1,5-diazabicyclo[4.3.0]non-5-ene), while the aprotic solvent may be toluene, hexane, benzene, tetrahydrofuran, dioxane, dialkyl ether, alkyl acetate, acetonitrile, acetone, dichloromethane, chloroform or carbon tetrachloride. As the solvent, a water-immiscible alcohol having four or more carbon atoms may also be used.

In the racemization reaction, the complex of Formula(I) of the present invention and the base may be used in amounts of $10^{-6}$ to 0.05 and $10^{-6}$ to 0.06 equivalent amounts, respectively, based on the chiral compound to be racemized.

The following Examples are included to further illustrate the present invention without limiting its scope.

Systhesis of Ruthenium Complexes

EXAMPLE 1

Synthesis of N-isobutylamino-2,3,4,5-tetraphenylcyclopentadienyl ruthenium dicarbonyl chloride Step 1) Synthesis of N-isobutyl-2,3,4,5-tetraphenylcyclopentadieneimine 3 g (7.8 mmol) of tetraphenylcyclopentadienone and 3.49 ml (35.1 mmol) of isobutylamine were dissolved in 50 ml of toluene and 0.7 ml(5.85 mmol) of $TiCl_4$ was added thereto at 0° C. The resulting mixture was agitated for 30 minutes at room temperature and then refluxed for 12 hours. The reaction mixture was cooled and ether was added thereto to induce solid precipitation. The resultant solid was filtered and dried to obtain 2.3 g of the title compound.

m.p.: 158° C;

$^1$H NMR($CDCl_3$): 7.25–7.18 (m, 10H), 7.09–7.00(m, 6H), 6.85(d, J=6.6 Hz, 2H), 6.78(m, J=6.6 Hz, 2H), 3.36(d, J=6.5 Hz, 8H), 1.83(m, 1H), 0.79(d, J=6.6 Hz, 2H)

Step 2) Synthesis of N-isobutylamino-2,3,4,5-tetraphenylcyclopentadienyl ruthenium dicarbonyl chloride 1 g (2.4 mmol) of the compound prepared in Step 1 and 1 g (1.6 mmol) of $Ru_3(CO)_{12}$ were dissolved in 8 ml of chloroform and reacted under an argon atmosphere at 90° C. for 5 days. The reaction mixture was cooled, concentrated and the residue was purified by column chromatography (column: silica gel, eluent: from hexane/ethylacetate of 8:1 to dichloromethane; gradient) to obtain 0.7 g of the title compound m.p.: 151~152° C. (dec.);

$^1$H NMR($CDCl_3$): 7.58–7.56(m, 4H), 7.38–7.33(m, 6H), 7.09(dd, J=7.1 Hz, 2H), 7.02–7.91(m, 8H), 4.36(t, J=5.7 Hz, 1H), 2.56(t, J=6.4, 2H), 1.39(m, 1H), 0.57(d, J=6.7 Hz, 6H);

$^{13}$C NMR($CDCl_3$): 198.6, 144.1, 133.7, 132.1, 130.7, 130.6, 129.1, 128.9, 128.4, 127.9, 101.6, 83.7, 52.1, 29.3, 20.1

EXAMPLE 2

Synthesis of N-isopropylamino-2,3,4,5-tetraphenylcyclopentadienyl ruthenium dicarbonyl chloride Step 1) Synthesis of N-isopropyl-2,3,4,5-tetraphenylcyclopentadieneimine The procedure of Step1 of Example 1 was repeated using 2.1 g of isopropylamine in place of isobutylamine to prepare the title compound.

m.p.: 223° C.;

$^1$H NMR($CDCl_3$): 7.25–6.75 (m, 20H), 4.08–4.00 (m, 1H), 1.04(d, J=3 Hz, 6H);

$^{13}$C NMR($CDCl_3$): 165.8, 137.6, 131.9, 130.2, 129.8, 128.2, 127.8, 127.4, 127.2, 127.1, 126.5, 52.3, 24.3

Step 2) Synthesis of N-isopropylamino-2,3,4,5-tetraphenylcyclopentadienyl ruthenium dicarbonyl chloride The procedure of Step2 of Example 1 was repeated using the compound prepared in Step1 to prepare the title compound.

m.p.: 197° C. (dec.);

$^1$H NMR($CDCl_3$): 7.57–6.91(m, 20H), 4.20(d, J=4.1 Hz, 1H), 3.3–3.23(m,1H), 0.86(d, J=3.2 Hz, 6H);

$^{13}$C NMR($CDCl_3$): 198.4, 144.8, 133.7, 131.9, 130.6, 128.9, 128.7, 128.2, 127.7, 101.4, 81.7, 45.6, 25.2

EXAMPLE 3

Synthesis of N-isobutylamino-2,3,4,5-tetraphenylcyclopentadienyl ruthenium dicarbonyl hydride 90 mg (0.14 mmol) of N-isopropyl-2,3,4,5-tetrabutylcyclopentadienyl ruthenium dicarbonyl chloride prepared in Example 1 and 45 mg (0.42 mmol) of sodium carbonate were dissolved in 6 ml of isopropanol and reacted at 90° C. for 5 hours. The reaction mixture was filtered and the filtrate was concentrated to prepare 83 mg of the title compound.

m.p.: 86.7° C. (dec.);

$^1$H NMR($C_6D_6$): 7.77(d, J=6.8 Hz, 4H), 7.57–7.54(m, 4H), 7.22–7.16(m, 8H), 7.04–7.01(m, 6H), 3.17(t, J=6.9 Hz, 1H), 2.66(t, J=6.5 Hz, 2H), 1.49(m, 1H), 0.82(d, J=6.5 Hz, 6H);

$^{13}$C NMR($C_6D_6$): 203.6, 133.9, 133.7, 132.9, 131.7, 129.2, 129.0, 128.7, 106.6, 92.1, 61.2, 29.2, 20.8

EXAMPLE 4

Synthesis of N-isopropylamino-2,3,4,5-tetraphenyl-cyclopentadienyl ruthenium dicarbonyl hydride The procedure of Example 3 was repeated using N-isopropyl-2,3,4,5-tetrapropylcyclopentadienyl ruthenium dicarbonyl chloride prepared in Example 2 to prepare the title compound.

m.p.: 140° C. (dec.);

$^1$H NMR(C$_6$D$_6$): 7.57–6.73(m, 20H), 2.99–2.93(m, 1H), 2.57(d, J=4.6 Hz, 1H), −9.14(s, 1H);

$^{13}$C NMR(C$_6$D$_6$): 203.6, 134.1, 133.4, 132.9, 132.8, 130.2, 129.0, 127.8, 127.1, 106.3, 91.0, 50.1, 21.9

Racemization of Chiral Secondary Alcohol Using Ruthenium Complexes of the Present Invention

EXAMPLE 5

1 mg of potassium t-butoxide, 6 mg of N-isobutylamino-2,3,4,5-tetrabutylcyclopentadienyl ruthenium dicarbonyl chloride prepared in Example 1 and 30 μl of (S)-1-phenylethanol (>99% ee) were dissolved in 1 ml of toluene and was agitated at room temperature for 30 minutes under an argon atmosphere. The reaction mixture was filtered and the filtrate was concentrated. The optical purity of the product measured with a HPLC(High Performance Liquid Chromatograph) equipped with a chiral column was 2% ee.

EXAMPLE 6

0.5 μl of 0.5 M Na$_2$CO$_3$, 6 mg of N-isobutylamino-2,3,4,5-tetraphenylcyclopentadienyl ruthenium dicarbonyl hydride prepared in Example 3 and 30 μl of (S)-1-phenylethanol (>99% ee) were dissolved in 1 ml of toluene and the procedure of Example 5 was repeated. The optical purity after the reaction was 11% ee.

EXAMPLE 7

1 mg of potassium t-butoxide, 6 mg of N-isopropylamino-2,3,4,5-tetraphenylcyclopentadienyl ruthenium dicarbonyl chloride prepared in Example 2 and 30 μl of (S)-1-phenylethanol (>99% ee) were dissolved in 1 ml of one of the solvents listed in Table 1 and agitated for 30 minutes at room temperature under an argon atmosphere. The optical purity measured as in Example 5 is shown in Table 1.

TABLE 1

| Solvent | Reaction time(hours) | Optical purity(% ee) |
|---|---|---|
| Toluene | 0.5 | 0.0 |
| methylene chloride | 0.5 | 0.0 |
| tetrahydrofuran | 0.5 | 0.0 |
| Acetone | 0.5 | 24.7 |
| toluene + vinyl acetate mixture(22:1) | 1.0 | 6.8 |
| No solvent | 12.0 | 1.6 |

EXAMPLE 8

The procedure of Example 6 was repeated using N-isopropylamino-2,3,4,5-tetraphenylcyclopentadienyl ruthenium dicarbonyl hydride prepared in Example 4. The optical purity after the reaction was 1.2% ee.

As the above results show, the ruthenium complexes of Formula(I) according to the present invention can racemize a chiral secondary alcohol rapidly at room temperature in the absence of a hydrogen-transfer agent.

While the invention has been described with respect to the specific embodiments, it should be recognized that various modifications and changes may be made by those skilled in the art to the invention which also fall within the scope of the invention as defined by the appended claims.

What is claimed is:

1. A ruthenium complex of Formula(I):

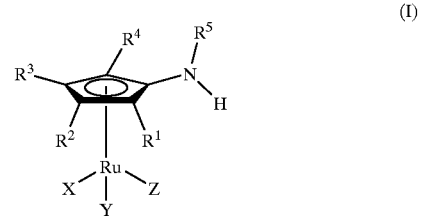

wherein:
R$^1$, R$^2$, R$^3$ and R$^4$ are each independently phenyl, substituted phenyl or C$_{1-5}$ alkyl;
R$^5$ is hydrogen, phenyl, substituted phenyl, C$_{1-5}$ alkyl, substituted C$_{1-5}$ alkyl, C$_{3-7}$cycloalkyl, C$_{2-5}$ alkenyl or C$_{2-5}$ alkynyl; and
X, Y and Z are each independently hydrogen, halogen, carbonyl or PR$^5$$_3$.

2. The ruthenium complex of claim 1, wherein the substituent of the substituted phenyl is at least one selected from the group consisting of C$_{1-5}$ alkyl, cycloalkyl, alkenyl, alkynyl, alkoxy, halogen, nitro, nitroso, amino, aminocarbamyl, hydroxy, mercapto and C$_{1-5}$ alkylthio and the substituent of the substituted C$_{1-5}$ alkyl is at least one selected from the group consisting of aryl, C$_{1-5}$ alkoxy, halogen, nitro, nitroso, amino, aminocarbamyl, hydroxy, mercapto and C$_{1-5}$ alkylthio.

3. The ruthenium complex of claim 1, wherein R$^1$, R$^2$, R$^3$ and R$^4$ are each phenyl or C$_{1-5}$ alkyl; R$^5$ is hydrogen, phenyl, C$_{1-5}$ alkyl or C$_{3-7}$ cycloalkyl; and X, Y and Z substituents are each independently hydrogen, halogen, carbonyl or phosphine.

4. A process for the preparation of the ruthenium complex of claim 1, which comprises reacting a compound of Formula(II) and a ruthemium compound selected from the group of Ru$_3$(CO)$_{12}$, RuCl$_2$(CO)$_2$(PR$^5$$_3$)$_2$, [RuCl$_2$(CO)$_3$]$_2$, RuCl$_2$(PR$^5$$_3$)$_3$, and RuCl$_3$ in a solution containing a haloform:

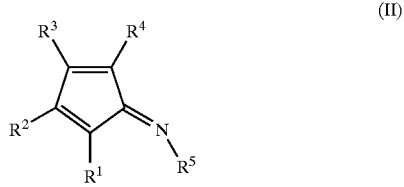

wherein:

R¹, R², R³, R⁴ and R⁵ have the same meanings as defined in claim 1.

5. The process of claim 4, wherein the compound of Formula(II) is obtained by reacting a cyclopentadienone in an aprotic solvent in the presence of a primary amine and a Lewis acid.

6. The process of claim 4, wherein the primary amine, the Lewis acid and the aprotic solvent are used in amounts of 1 to 7 molar equivalents, 0.1 to 3 molar equivalents and 2 to 20 folds (v/v), respectively, based on the compound of Formula(II).

7. The process of claim 6, wherein the reaction is conducted at a temperature in the range of 50° C. to 150° C.

8. The process of claim 4, wherein the compound of Formula(II) and the ruthenium compound are used in a molar ratio ranging from 1:1 to 3:1.

9. The process of claim 4, wherein the reaction is conducted at a temperature in the range of 40° C. to 120° C.

10. A process for the racemization of a chiral compound, which comprises reacting the chiral compound with the complex of claim 1 in the presence of a base.

11. The process of claim 10, wherein the chiral compound is a secondary alcohol.

\* \* \* \* \*